United States Patent [19]

Hisamoto et al.

[11] Patent Number: 4,638,089

[45] Date of Patent: Jan. 20, 1987

[54] FLUORINE-CONTAINING QUATERNARY AMMONIUM COMPOUNDS AND THEIR PRODUCTION

[75] Inventors: Iwao Hisamoto, Osaka; Chiaki Maeda, Kyoto; Mitsuhiro Nishiwaki, Osaka, all of Japan

[73] Assignee: Daikin Kogyo Co., Ltd., Osaka, Japan

[21] Appl. No.: 257,194

[22] Filed: Apr. 24, 1981

[30] Foreign Application Priority Data

Apr. 26, 1980 [JP] Japan .................................. 55-56049

[51] Int. Cl.[4] .............................................. C07C 91/26

[52] U.S. Cl. .................................... 564/292; 564/285; 564/280; 560/252; 560/253; 260/501.15

[58] Field of Search ................ 560/252, 253; 564/280, 564/292, 285; 260/501.15

[56] References Cited

U.S. PATENT DOCUMENTS

| | | | |
|---|---|---|---|
| 2,653,156 | 9/1953 | Deutsch et al. | 560/253 |
| 3,989,711 | 11/1976 | Bodor | 560/253 |
| 4,128,485 | 12/1978 | Bauman et al. | 560/253 |
| 4,377,710 | 3/1983 | Seale et al. | 564/281 |

FOREIGN PATENT DOCUMENTS 1330203 9/1973 United Kingdom ................ 560/253

OTHER PUBLICATIONS

Weygand et al, Preparative Organic Chemistry, 1972, pp. 448 and 457.

*Primary Examiner*—James H. Reamer

*Attorney, Agent, or Firm*—Birch, Stewart, Kolasch & Birch

[57] ABSTRACT

A fluorine-containing quaternary ammonium compound of the formula:

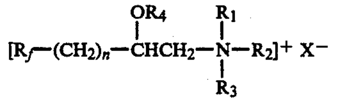

wherein $R_f$ is a fluorine-containing straight or branched aliphatic hydrocarbon or polyether group, $R_1$, $R_2$ and $R_3$ are each a $C_1$-$C_{21}$ straight or branched alkyl, hydroxyalkyl or alkenyl group or a substituted or unsubstituted aryl or aralkyl group, $R_4$ is a hydrogen atom or a acyl group, $X^-$ is an anion and n is an integer of 1 to 3, having a capability of reducing the surface tension of water and the interfacial tension between water and oil.

10 Claims, No Drawings

FLUORINE-CONTAINING QUATERNARY AMMONIUM COMPOUNDS AND THEIR PRODUCTION

BACKGROUND OF THE INVENTION

The present invention relates to fluorine-containing quaternary ammonium compounds and their production. More particularly, it relates to fluorine-containing quaternary ammonium compounds which are effective in reducing the surface tension of water as well as the interfacial tension between water and oil, and their production.

In general, fluorine-containing compounds can reduce the surface tension of water and are useful as evaporation-preventing agents, leveling agents, etc. On the other hand, there are considerable demands for additives to aqueous foam fire-extinguishing agents. Since such fire-extinguishing agents are necessitated to spread quickly over an oil surface to form an aqueous film, the said additives are required to have not only a capability of reducing the surface tension but also a capability of reducing the interfacial tension between water and oil. Namely, the spreading coefficient (S) has the following relationship with the surface tension of oil ($\gamma_o$), the surface tension of water ($\gamma_w$) and the interfacial tension between water and oil ($\gamma_{wo}$): $S=\gamma_o-(\gamma_w+\gamma_{wo})$, and water can spread over the oil surface only when S is positive. Unfortunately, however, the fluorine-containing group in conventional fluorine-containing compounds has only a low affinity to oil so that the satisfactory orientation at the interface between water and oil can not be attained. Thus, conventional fluorine-containing compounds can not sufficiently reduce the interfacial tension between water and oil. In order to supplement such insufficiency, the simultaneous use of a hydrocarbon compound surfactant is thus necessary.

Japanese Patent Publication (examined) No. 21133/1974 discloses amines having a fluoroalkyl group and their salts with organic or inorganic acids. While they are quite effective in reducing the surface tension of water, their capability of reducing the interfacial tension between water and oil is still not satisfactory. For using them practically as additives to aqueous foam fire-extinguishing agents, their activity for reducing the interfacial tension between water and oil must be enhanced by any appropriate means.

SUMMARY OF THE INVENTION

As the result of an extensive study, it has now been found that certain fluorine-containing quaternary ammonium compounds have a sufficient capability of reducing the surface tension of water and the interfacial tension of water and oil and can play, by themselves, a satisfactory role as additives to aqueous foam fire-extinguishing agents.

DETAILED DESCRIPTION

According to the present invention, there is provided a fluorine-containing quaternary ammonium compound of the formula:

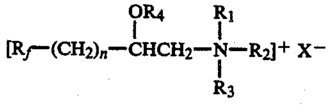

(I)

wherein $R_f$ is a fluorine-containing aliphatic hydrocarbon or polyether group, $R_1$, $R_2$ and $R_3$ are each an alkyl, hydroxyalkyl or alkenyl group or a substituted or unsubstituted aryl or aralkyl group, $R_4$ is a hydrogen atom or an acyl group, $X^-$ is an anion and n is an integer of 1 to 3.

The fluorine-containing aliphatic hydrocarbon group represented by $R_f$ may be a straight or branched, saturated or unsaturated one, usually having not more than 21 carbon atoms. The fluorine-containing aliphatic polyether group represented by $R_f$ has usually not more than 20 carbon atoms and may be the one of the formula:

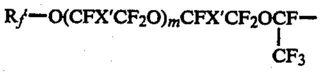

wherein $R_f'$ is a $C_1$-$C_3$ perfluoroalkyl group, X' is a fluorine atom or a trifluoromethyl group and m is an integer of 0 to 4.

The substituents represented by $R_1$, $R_2$ and $R_3$ may be straight or branched ones having not more than 21 carbon atoms. The acyl group represented by $R_4$ may be the one having not more than 4 carbon atoms (e.g. acetyl, propionyl, butyryl).

Specific examples of the anion $X^-$ are anions of halide, hydroxylate, alkoxylate, carboxylate, phenoxide, sulfonate, sulfate, sulfite, phosphate, carbonate, alkylsulfate, alkylsulfite, etc.

The fluorine-containing quaternary ammonium compound (I) may be prepared by reacting a fluorine-containing amine of the formula:

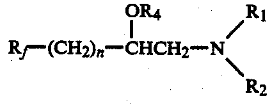

(II)

wherein $R_f$, $R_1$, $R_2$, $R_4$ and n are each as defined above with a quaternizing agent of the formula:

$R_3X$ wherein $R_3$ and X are each as defined above.

The fluorine-containing amine (II) in which $R_4$ is hydrogen can be prepared by the process as disclosed in Japanese Patent Publication (examined) No. 21123/1974. The fluorine-containing amine (II) in which $R_4$ is acyl (e.g. acetyl, propionyl, butyryl) is obtainable by treating the corresponding amine (II) in which $R_4$ is hydrogen with an acylating agent such as an acid anhydride or an acid halide.

The reaction is usually carried out in the presence of a solvent at a temperature of from room temperature to 100° C. for 1 to 5 hours under stirring. Preferably, the quaternizing agent is used in an equimolar amount or more to the fluorine-containing amine (II). Examples of the solvent are a lower alkanol (e.g. methanol, ethanol, isopropanol), acetone, tetrahydrofuran, etc.

Some typical examples of the reaction are representable by the following formulas:

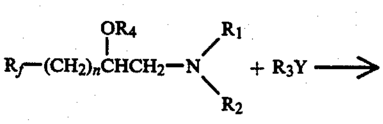

-continued

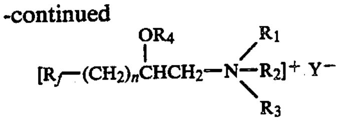

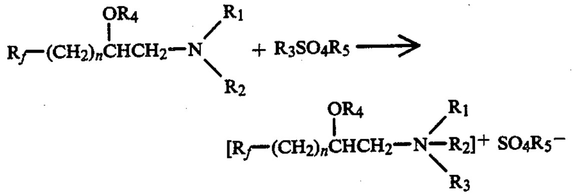

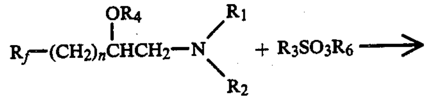

-continued

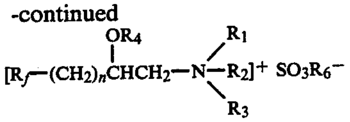

wherein $R_5$ is a $C_1$–$C_3$ alkyl group, $R_6$ is a $C_1$–$C_3$ alkyl group or a substituted or unsubstituted phenyl group, Y is chlorine, bromine or iodine and $R_f$, $R_1$, $R_2$, $R_3$ and $R_4$ are each as defined above.

After completion of the reaction, the recovery of the product may be effected in a per se conventional procedure. For instance, the solvent is distilled off from the reaction mixture, and the residue is purified by washing with a solvent such as ether or by crystallization.

Specific examples of the thus produced fluorine-containing quaternary ammonium compounds (I) are as follows:

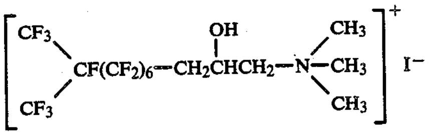

(III)

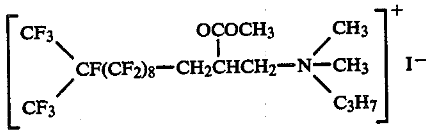

(IV)

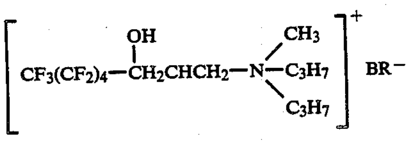

(V)

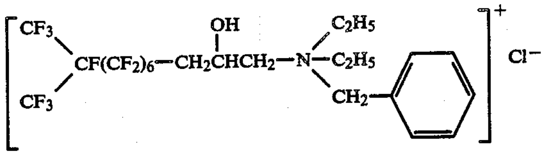

(VI)

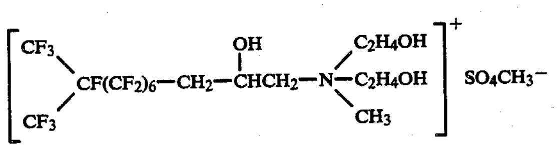

(VII)

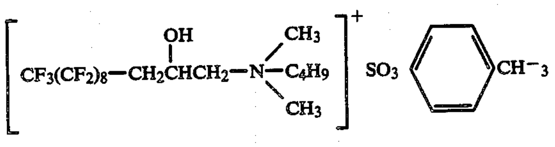

(VIII)

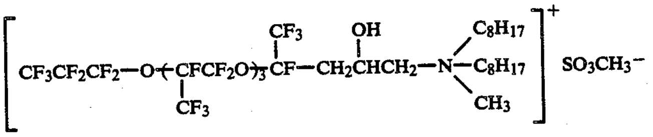

(IV)

-continued

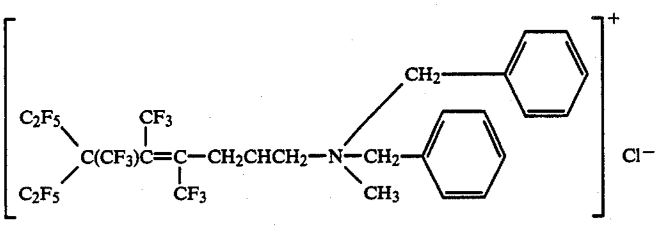

(X)

The fluorine-containing quaternary ammonium compound (I) has a low critical micelle concentration and can effectively reduce the surface tension of water as well as the interfacial tension between water and oil even when used in such a low concentration as 0.01% by weight.

On the use of the fluorine-containing quaternary ammonium compound (I) as a surfactant, any fluorine-containing cationic, nonionic or amphoteric surfactant may be incorporated therein. Examples of them are perfluoroalkylalkylene trialkylammonium halides, perfluoroalkanesulfonamidealkylene trialkylammonium halides, $$R_f''-O(CH_2CH_2O)_pH,\ R_f''-\overset{\overset{O}{\|}}{C}O(CH_2CH_2O)_pH$$

(wherein $R_f''$ is a fluorine-containing aliphatic hydrocarbon group and p is an integer of 1 to 40), perfluoroalkylalkylenedialkylaminoacetic acid betaine, perfluoroalkanesulfonamidoalkylenedialkylaminopropionic acid betaine, etc.

Any hydrocarbon compound surfactant may be also incorporated into the fluorine-containing quaternary ammonium compound (I). Examples of the hydrocarbon compound surfactant are nonionic ones (e.g. polyoxyethylenealkyl ether, polyoxyethylene fatty acid ester), cationic ones (e.g. tri alkylammonium halide, benzalkonium chloride), trialkylaminoacetic acid betaine, alkylglycine, etc.

The fluorine-containing quaternary ammonium compounds (I) of the invention are useful as evaporation preventing agents, leveling agents, additives for protein foam fire-extinguishing agents or synthetic surfactant foam fire-extinguishing agents, dry chemical fire-extinguishing agents, additives for photographic emulsions, mist loss reducing agents for plating baths, etc.

The present invention will be illustrated more in detail with reference to the following examples wherein part(s) and (%) are by weight.

PREFERRED EMBODIMENTS

EXAMPLE 1

Production of the compound (III):

Into a 200 ml flask equipped with a stirrer and a cooler, $(CF_3)_2CF(CF_2)_6CH_2CH(OH)CH_2N(CH_3)_2$ (20.0 g, 0.035 mol), methyl iodide (6.0 g, 0.042 mol) and ethanol (70 g) are charged, and the resulting mixture is stirred on a hot water bath under refluxing for 2 hours. The reaction mixture is cooled, and ether is added thereto. The precipitated substance is collected and washed with ether to give the compound (III) (21.5 g; yield, 86%) having a melting point of 40°–42° C.

The standard bromophenol blue test shows that the said substance is a cationic quaternary ammonium compound.

EXAMPLE 2

Production of the compound (VII):

Into the same reaction apparatus as in Example 1, $(CF_3)_2CF(CF_2)_6CH_2CH(OH)CH_2N(C_2H_4OH)_2$ (20.0 g, 0.032 mol), dimethylsulfate (4.8 g, 0.038 mol) and ethanol (70 g) are charged, and the resulting mixture is stirred on a hot water bath under refluxing for 1 hour. The solvent is evaporated off. The obtained solid substance is washed with ether to give the compound (VII) (22.0 g; yield, 91.7%) having a melting point of 101°–103° C.

The standard bromophenol blue test shows that the said substance is a cationic quaternary ammonium compound.

EXAMPLE 3

Production of the compound (VI):

Into the same reaction apparatus as in Example 1, $(CF_3)_2CF(CF_2)_6CH_2CH(OH)CH_2N(C_2H_5)_2$ (20.0 g, 0.03 mol), benzyl chloride (6.3 g, 0.050 mol) and isopropanol (70 g) are charged, and the resulting mixture is stirred on a hot water bath under refluxing for 4 hours. The solvent is evaporated off. The obtained solid substance is washed with ether to give the compound (VI) (19 g; yield, 79.4%) having a melting point of 50°–52° C.

The standard bromophenol blue test shows that the said substance is a cationic quaternary ammonium compound.

REFERENCE EXAMPLE

With the compounds (III) to (VIII) prepared in Examples 1 to 3 or in the procedure similar thereto, the surface tension of the 0.1% aqueous solution and the interfacial tension between such aqueous solution and n-hexane were measured by the use of the ST-1 type apparatus (manufactured by Shimadzu Seisakusho K.K.) according to the Wilhelmy method at 25° C. For comparison, the surface tension and the interfacial tension were also measured on some fluorine-containing amine compounds neutralized with acids. The results are shown in Table 1.

TABLE 1

| Compound | Surface tension (dyne/cm) | Interfacial tension (dyne/cm) |
|---|---|---|
| (III) | 17.0 | 4.8 |
| (IV) | 17.0 | 5.0 |
| (V) | 18.0 | 5.7 |
| (VI) | 17.0 | 4.9 |
| (VII) | 17.5 | 5.0 |
| (VIII) | 17.5 | 5.5 |
| Comparative Example 1*1 | 19.0 | 10.2 |
| Comparative Example 2*2 | 18.5 | 8.4 |
| Comparative | 18.0 | 11.0 |

TABLE 1-continued

| Compound | Surface tension (dyne/cm) | Interfacial tension (dyne/cm) |
|---|---|---|
| Example 3*3 | | |

Note:
*1 Neutralized compound of $(CF_3)_2CF(CF_2)_6CH_2CH(OH)CH_2N(CH_3)_2$ with acetic acid
*2 Neutralized compound of $(CF_3)_2CF(CF_2)_6CH_2CH(OH)CH_2N(CH_3)_2$ with hydrochloric acid
*3 Neutralized compound of $CF_3(CF_2)_8CH_2CH(OH)CH_2N(C_3H_7)_2$ with formic acid

What is claimed is:

1. A fluorine-containing quaternary ammonium compound of the formula:

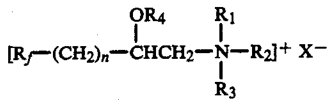

wherein $R_f$ is a fluorine-containing aliphatic hydrocarbon or polyether group, $R_1$, $R_2$ and $R_3$ are each an alkyl, hydroxyalkyl alkenyl group aryl or aralkyl group, $R_4$ is a hydrogen atom or an acyl group, $X^-$ is an anion and n is an integer of 1 to 3.

2. The compound according to claim 1, wherein $X^-$ is an anion of halide, hydroxylate, alkoxylate, carboxylate, phenoxide, sulfonate, sulfate, sulfite, phosphate, carbonate, alkylsulfate or alkylsulfite.

3. The compound according to claim 1, wherein $X^-$ is chlorine, bromine, iodine, $SO_4R_5$ in which $R_5$ is a $C_1$-$C_3$ alkyl group or $SO_3R_6$ in which $R_6$ is a $C_1$-$C_3$ alkyl group or a substituted or unsubstituted phenyl group.

4. The compound according to claim 1, wherein $R_f$ is a fluorine-containing straight or branched, saturated or unsaturated aliphatic hydrocarbon group having not more than 21 carbon atoms.

5. The compound according to claim 1, wherein $R_f$ is a fluorine-containing aliphatic polyether group having not more than 20 carbon atoms.

6. The compound according to claim 5, wherein the fluorine-containing aliphatic polyether group is a group of the formula:

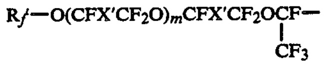

in which $R_f'$ is a $C_1$-$C_3$ perfluoroalkyl group, X' is a fluorine atom or a trifluoromethyl group and m is an integer of 0 to 4.

7. The compound of claim 4, wherein said fluorine-containing quaternary ammonium compound is

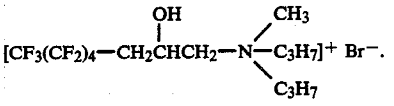

8. A composition represented by the formula:

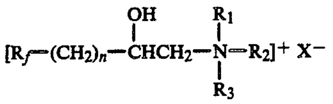

wherein $R_f$ is a perfluorinated polyether group, $R_1$, $R_2$ and $R_3$ are each an alkyl group having not more than 21 carbon atoms or an aryl group with the proviso that at least two of $R_1$, $R_2$ and $R_3$ are methyl or ethyl; $X^-$ is a halogen anion chosen from the group consisting of chloride, bromide and iodide and n is 1.

9. The composition of claim 8, wherein $R_1$, $R_2$ and $R_3$ are each methyl radicals and $X^-$ represents a chlorine anion.

10. The composition of claim 8, wherein $R_1$ and $R_2$ are each chosen from the group consisting of methyl and ethyl hydrocarbon radicals and $R_3$ is an aryl group.

* * * * *